United States Patent [19]

Riethorst et al.

[11] Patent Number: 4,883,598

[45] Date of Patent: Nov. 28, 1989

[54] PROCESS FOR ISOLATING COAGULATION FACTORS, AND ADSORBENT MATERIAL SUITABLE THEREFOR

[75] Inventors: Waander Riethorst, Walkottelanden 92, 7542 MV Enschede; Bondewyn W. König, Maarssenbroeck; Willem G. van Aken, Amstevlveen; Adriaan Bantjes, Enschede; Tom Beugeling, Enschede; Marcelinus P. W. M. Te Booy, Amsterdam, all of Netherlands

[73] Assignee: Waander Riethorst, Netherlands

[21] Appl. No.: 227,681

[22] Filed: Aug. 3, 1988

[30] Foreign Application Priority Data

Aug. 14, 1987 [NL] Netherlands ........................ 8701915

[51] Int. Cl.$^4$ ............................................. B01D 15/08
[52] U.S. Cl. .................................. 210/656; 210/198.2; 210/502.1; 210/691; 210/692; 502/402; 502/404; 530/381; 530/413; 536/18.7
[58] Field of Search ...................... 210/656, 905, 198.2, 210/679, 502.1, 691, 692; 530/383, 384, 381, 413, 415, 417, 382; 424/101; 536/101, 18.7; 502/401, 402, 404

[56] References Cited

U.S. PATENT DOCUMENTS

| | | | |
|---|---|---|---|
| 3,947,352 | 3/1976 | Cuatvecasas et al. | 502/404 |
| 4,086,222 | 4/1978 | Lindquist et al. | 520/383 |
| 4,090,919 | 5/1978 | Chibata et al. | 210/679 |
| 4,663,163 | 5/1987 | Hou et al. | 210/656 |

*Primary Examiner*—W. Gary Jones
*Attorney, Agent, or Firm*—Peter L. Michaelson, Esq.

[57] ABSTRACT

This invention relates to a process and to absorbent material for isolating coagulation factors, including FVIII and vWF, from the example blood plasma and plasma products by means of liquid chromatography. The adsorbent material comprises a polymeric carrier to which amino groups are linked as ligands through spacers. The spacers have a chain length of at least 6 atoms and contain at least one hydrophilic link within the chain. The spacers preferably have the formula $-(CH_2)_m-CO-NH-(CH_2)_n-$ wherein m and n each represent an integer of 1–6 and m+n is at least 4. The spacers are preferably linked to the carrier through $-CO-NH-$ groups. The ligand density in the absorbent material is preferably higher than 30 umoles/ml of swollen matrix.

20 Claims, No Drawings

PROCESS FOR ISOLATING COAGULATION FACTORS, AND ADSORBENT MATERIAL SUITABLE THEREFOR

This invention relates to a process for isolating coagulation factors, such as, in particular, the coagulation factors FII, FVII, FVIII, FIX, FX and the Von Willebrand factor (vWF, in the literature sometimes designated by FVIIIR) from a starting material such as blood plasma, plasma products, cell lysates and fermentation or culture mediums by means of liquid chromatography.

The invention also relates to an adsorbent material for use therein, which will sometimes be designated herein by the terms affinity matrix, hydrogel or gel, and which adsorbent material comprises a polymeric carrier material to which, through spacers, ligands are linked, consisting of terminal primary, secondary, tertiary or quaternary amino groups.

The blood of human beings and animals contains small quantities of various substances involved in the blood coagulation or blood clotting process. For various reasons there is a need for methods by which these substances can be isolated in as high a yield as possible and a purity as high as possible from the blood (or any other suitable starting material). Thus, for example, the protein factor VIII occurring in blood plasma (sometimes designated in the literature as FVIII) is one of the thirteen clotting factors necessary for an effective blood coagulation process. In about 1,000 people (hemophilia A patients) in The Netherlands, this clotting factor is fully or partially absent or inoperative, so that their blood is incapable of clotting normally. Hemophilia can be treated with factor VIII preparations which can be prepared from human donor blood. As the yields of existing methods of preparation are very low (<40%) and the demand for preparations is increasing, there is a shortage of factor VIII throughout the world.

Various methods are known for isolating FVIII and/or other clotting factors and proteins by means of liquid chromatography from a blood-based starting material. Some of these known methods use conventional anion exchangers for this purpose, such as DEAE cellulose and DEAE Sephadex; others employ certain polyelectrolytes; and still others apply modified Sepharoses. These various known methods will be considered in more detail below.

Conventional Anion Exchangers

The conventional anion exchangers, such as DEAE cellulose and DEAE Sephadex, were used several times in the purification of factor VIII concentrates in the 'sixties. They are (more or less obsolete) matrices to which a substituted diamine (diethyl-amino-ethylamine) is coupled by well-known, much used coupling methods. The use of these materials for the factor VIII purification and isolation, however, was discontinued owing to a number of disadvantages of these gels, as a result of which they were little used over the last few years. Literature: Thromb.Diath. Haemorrh. 3 (1959) 572; 4(1960) 211; 6 (1961) 282; 16 (1966) 738–751.

Polyelectrolytes EMA PE-5 and PE-100

The EMA polyelectrolytes introduced by Johnson in the 'seventies also consist of a polymeric material to which a diamine (dimethyl-amino-propylamine) is coupled and thus also belong to the anion exchangers. The ligand density is rather high and differs per polyelectrolyte. The selected matrix (a copolymer of ethylene and maleic acid anhydride) is rather unusual. An essential feature in the chemical structure is the N,N-dimethylaminopropylamide group, which owing to its weakly basic character (pKa=5.4) is partially positively charged at pH 6–7. Two different polyelectrolytes are used:

(1) PE-100—in which virtually 100% of the maleic acid anhydride units are substituted with the amine. At pH 8.0 the coagulation factors II, VII, IX and X can be adsorbed with it from plasma, and, after washing the polyelectrolyte, eluted at pH 6 with 1.5 M sodium chloride. The supernatant is contacted with PE-5.

(2) PE-5—in which 5% is substituted. At pH 6, the FVIII:C is adsorbed, whereas vWF remains in solution. After washing the PE-5, FVIII:C can be eluted at pH 7.4 with 1.0M lysine/1.5M sodium chloride with a yield of 43% and a 52-fold purification. By contacting the supernatant again (other conditions) with PE-100 (pH 6.0), vWF, too, can be isolated with a yield of 43% and in a 71-fold purification.

From the experiments, the conclusion was drawn that FVIII initially binds to the EMA PE by electrostatic interaction, whereafter hydrofobic interaction strengthens the bond. This renders elution difficult, so that the yield is relatively low. Furthermore, it turns out that lysine has a stabilizing effect, that the yield can be increased by adding heparin, and that during the process the Hepatitis B virus titer is decreased.

As neither the blood contact properties, nor the mechanical properties of these EMA polyelectrolites are good (activation of coagulation, high a specific adsorption, poor throughflow and poorly suspended) they have mainly been used for the isolation of FVIII from porcine plasma or the purification of cryoprecipitates. Literature: J.Lab. Clin. Med. 92 (1978) 194–210; U.S. Pat. Nos. 4,397,841; 4,471,112.

Modified Sepharoses

The AH-Sepharose (aminohexyl-Sepharose) having general formula (Sepharose—O—C(=NH)—NH—(CH$_2$)$_6$—NH$_2$ was initially introduced by Pharmacia for the immobilisation of proteins by covalent bonding of the amine with carboxyl groups of the protein. Owing to the strongly basic character of this primary amine (pKa=9.9), however, the gel can also be classified among the anion exchangers and also behave as one.

For the separation of factor VIII this latter is apparent from a study published by Austen. With 8.6 ml AH-Sepharose 4B, the FVIII can be purified from FVIII concentrate (600 IU) 70 times (1.8 IU/mg) in a yield of about 35%. Adsorption takes place in 0.1M acetate/lysine, pH 5.5; and elution in this buffer with 0–1M sodium chloride. A separation between FVIII:C and vWF can be accomplished. The AH-Sepharose was prepared by coupling 1,6-hexane diamine to CNBr-activated Sepharose 4B by the Axen method, which gave a ligand density of about 7 umoles/ml. The bonding of FVIII to the gel appears to be electrostatic, although additional hydrophobic interaction cannot be excluded. It was also found that the Hepatitis B virus titer after purification was 1/60th of the initial value.

At the same time, butyl-Sepharose with the generic formula Sepharose—O—C(=NH)—NH—(CH$_2$)$_4$—H, was studied by Vukovich et al. This was prepared by coupling 1-butane amine to CNBr-activated Sepharose 4B. Plasma (10 ml) was diluted 5 times in 20 mM tris/1 mM citrate buffer, pH 7.4 and applied to the butyl-Sepharose column (20 ml). Thereby the coagulation factors II, V, VII, VIII, IX and X were bonded quantitatively. Elution was effected in the buffer with 0–2M sodium chloride. FVIII was eluted at 0.3–0.6M sodium chloride with about 60% yield and 23-fold purification, separated from the other coagulation factors. On the basis of the results, hydrofobic interaction of FVIII with butyl-Sepharose was concluded, and electrostatic interaction was fully excluded.

Subsequently, Morgenthaler did a systematic study to clarify the binding character of FVIII with various substituted Sepharoses. A homologous series of aminoalkyl-Sepharoses were made and tested under the same conditions (pH 5.5) as those of Austen. At the same time, a series of alkyl-Sepharoses were prepared which were investigated under these conditions and also under conditions suitable for hydrofobic interaction. Both series were prepared by coupling the amine in question to CNBr-activated Sepharose 4B.

With increasing chain length, more FVIII:C and protein were bonded to the aminoalkyl-Sepharoses, and these were eluted at higher sodium chloride concentrations. No FVIII:C could be eluted from aminoheptane and amino-nonane-Sepharose. The adsorption to the alkyl-Sepharoses did not differ significantly from that to the aminoalkylSepharoses. With an ethylene glycol gradient (0–50%) only little protein, but no FVIII:C could be eluted. By increasing the salt concentration, some protein with FVIII:C could thereafter be eluted from the shorter chains, which did not succeed with the longer chains. Hydrofobic interaction was considered responsible for the adsorption, while in the series of alkyl-Sepharoses electrostatic interaction was even fully excluded.

Both Vukovich and Morgenthaler assumed that the interaction of FVIII with the alkyl-Sepharoses used was based on hydrofobic interaction. This is inconsistent with the fact that they were able to accomplish elution at elevated sodium chloride concentration.

At the same time it has meanwhile turned out from both the literature and our own studies that electrostatic interaction with the alkyl-Sepharoses prepared through CNBr activation must not be excluded, because the coupling of the amine to the CNBr-activated Sepharose results in an isourea bond, which is weakly alkaline (pKa=8).

In summary, it can be concluded that FVIII:C exhibits interaction with (ar.ino)alkyl ligands, but that the character of this interaction is not quite clear. Furthermore, it is unknown whether the stronger bond to longer chains is caused by the fact that, in addition to being longer, these chains are also more hydrofobic, or just because they are better accessible to the larger FVIII:C molecule owing to less steric hindrance. Also, it has never been investigated what effect the "ligand density" has on the bonding of FVIII:C and other plasma proteins.

In addition to the importance of the knowledge about the bonding behaviour, which could possibly lead to the development of "better" binders, there is the importance of practical utility. Some literature has meanwhile appeared about this, mainly directed to AH-Sepharose.

Generally speaking, it can be stated that the pH of the buffer used has an effect on both the yield and the purity. The pH most frequently used was 5.5. Because at low pH the proteins generally have less negative charge, while the positive charge on the gel is not changed, less protein will adsorb than at higher pH. Because this appears to apply to a lesser extent to FVIII (low pI) this can enhance the specificity of the gel (higher purification). However, at low pH the FVIII:C is less stable, so that the yield becomes lower.

Faure et al. have sought the solution to this problem in the addition of stabilizers. Saccharose was added to prevent complexing of FVIII with FIXa and FX and hence prcteolysis. In plasma, however, this had little effect. From 224 ml plasma on 30 ml AH-Sepharose, the yield was about 40% with a 9-fold purification.

Amphlett has described an isolation from plasma at pH 6.8. Without the addition of stabilizer, the yield was 39% with a 32-fold purification. Adsorption was effected in 20 mM tris/0.1M lysine with 0.3M sodium chloride, pH 6.8, and elution was carried out in this buffer with 0.5M calcium chloride. When 0.5M benzamidine/0.1% trasylol was added—which possibly results in less proteolytic hydrolysis—the yield was 90% with an 48-fold purification.

Literature: Brit. J.Haematol. 43(1979) 669–674; Thromb. Haemost. 48(1982) 46–48; Folia Haematol., Leipzig 107 (1979) 148–151; Thromb. Haemostas. 47(1982) 124–127; J Chromat. 257(1983) 387–391; U.S. Pat. No. 4,508,709.

As appears from the above discussion of the prior art, all known processes have one or more disadvantages, sch as a low yield, poor purity and/or low stability of the isolated products.

The present invention provides a process for isolating-coagulation factors, and an adsorbent material for use therein, with which significant improvements are achieved, in particular an improvement in yield, purity, and/or stability, and also provides a new adsorbent material suitable for this purpose.

Thus the invention provides more in particular a process for isolating coagulation factors from a starting material such as blood plasma, plasma products, cell lysate and fermentation or culture mediums by means of liquid chromatography, which is characterized by using an adsorbent material comprising a polymeric carrier material to which ligands, consisting of primary, secondary, tertiary, or quaternary amino groups, are linked via spacers, said spacers having a chain length of at least 6 atoms and containing within the chain at least one link having hydrophilic properties.

As used herein, the term link having hydrophilic properties, or hydrophilic link means a group within, or element of, the chain.

The invention further provides an adsorbent material for use in the process, comprising a polymeric carrier material to which, via spacers, ligands are bonded, consisting of terminal primary, secondary, tertiary or quaternary amino groups, which adsorbent material is characterized in that the spacers have a chain length of at least 6 atoms and contain within the chain at least one link having hydrophilic properties.

For that matter, some adsorbent materials consisting of a polymeric carrier material to which amino groups are bonded via spacers having a chain length of at least 6 atoms and containing at least one hydrophilic link within the chain are known. Thus U.S. Pat. No. 4,090,919 discloses an aminoalkyl polysaccharide which can be obtained by reacting an alkylene diamine with a carboxymethyl polysaccharide and in which the side chains, which are linked to the polymeric carrier through an oxygen atom, have the generic formula —$CH_2$—CONH—$(CH_2)_m$—$NH_2$. That publication does not, however, refer to the use of such materials in a process for isolating coagulation factors, but the materials are proposed as a water-insoluble carrier for tannin. According to the specification, by bonding or adsorbing tannin to this carrier material, a water-insoluble tannin composition is obtained which can be used as an adsorbent for all sorts of proteins.

Furthermore, reference can be made to "Affinity Chromatography" by Lowe and Dean, 1974, pp. 218–220, in which various types of spacers are described. However, that publication, too, does not refer to an application of an adsorbent material as defined herein in a process for isolating coagulation factors.

In a preferred embodiment according to the present invention, the ligand density in the adsorbent material is higher than 30 umoles/ml of swollen matrix, more preferably higher than 50 umoles/ml and most preferably 60–100 umoles/ml of swollen matrix.

The invention accordingly also provides an adsorbent material suitable for use in the process described above, which is characterized by comprising a polymeric carrier material to which ligands, consisting of primary, secondary, tertiary, or quaternary amino groups, are linked via spacers, said spacers having a chain length of at least 6 atoms and containing within the chain at least one link having hydrophilic properties, the ligand density being higher than 30 umoles/ml of swollen matrix, preferably higher than 50 umoles/ml of swollen matrix.

A preferred embodiment of the adsorbent material according to the invention is characterized in that the spacers satisfy the generic formula 1:

$$-(CH_2)_m-CO-NH-(CH_2)_n- \quad (1)$$

in which m and n represent integers having a value of 1–6 and m+n at least equals 4.

Furthermore, it is preferable, and in accordance with the present invention, that the carrier material is a hydroxyl groups containing polymeric material to which the spacers are bonded through coupling groups having the formula 2:

$$-CO-NH- \quad (2)$$

The most preferred adsorbent material according to the invention can be represented by the generic formula 3:

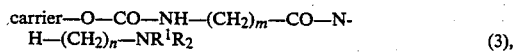

$$\text{carrier}-O-CO-NH-(CH_2)_m-CO-NH-(CH_2)_n-NR^1R^2 \quad (3),$$

where m and n have the meanings mentioned before, and $R^1$ and $R^2$, independently of each other, each represent a hydrogen atom or a substituted or unsubstituted hydrocarbon group, such as alkyl, cycloalkyl, aryl, aralkyl, etc.

Preferably, the carrier material is an agarose, such as Sepharose CL 4B.

It is also preferable that the ligands consist of primary amino groups, i.e. that $R^1$ and $R^2$ in the above generic formula 3 represent hydrogen atoms.

In the process according to the invention, it is preferable that, in the adsorption step, an equilibration buffer and liquid starting material with a specific conductivity of below 20 mS/cm, preferably 13–16 mS/cm, are used.

A further preferred feature is that a volume ratio of matrix:starting material of less than 1:8, most preferably 1:12 to 1:20 is used.

It is also preferred that elution is realized by increasing the conductivity of the buffer, preferably by means of sodium chloride.

As regards the pH, preferably a pH in the range of 6–8, most preferably about 7, is maintained.

The advantages offered by the invention in isolating coagulation factors are the unexpected result of the use of spacers between the amino groups functioning as ligands and the carrier material, which spacers are equally long or longer than those of the well-known aminohexyl-Sepharose, but more hydrophilic or not more hydrofobic, due to the presence within the spacer of a link having hydrophilic properties, such as the —CO—NH—link.

By using a relatively long spacer, compared with the known materials for the purification of coagulation factors, such as DEAE-Sephadex, DMAP-EMA (Johnson), AH-Sepharose and aminobutyl-Sepharose, a higher adsorption capacity for the FVIII-vWF complex is obtained with the same ligand density. As a consequence, the adsorption of the desired proteins is more specific, and a purer product can be obtained.

By using a relatively hydrophilic spacer (less than 6 linked methylene groups), compared with e.g. AH-Sepharose, with the same adsorption capacity (i.e., possibly a lower ligand density) the adsorption is more specific, while at the same time the elution of FVIII-vWF is better (higher yield, better reproducible). As a consequence, a purer product can be obtained in a higher yield.

The carrier in the adsorbent material according to the invention is preferably an agarose, such as Sepharose CL 4B, but is not restricted to such a polymeric material. Preferably, the carrier satisfies the following requirements:

1. the carrier generally causes only minimum interaction with the plasma proteins. This applies both during adsorption to promote the specificity of the affinity matrix and during elution to increase the yield;

2. the carrier possesses a very wide-meshed pore structure with a large internal surface area. This promotes a high adsorption capacity;

3. the carrier is both chemically and physically highly stable. This is desirable in connection with the coupling of the ligand, the possibility of regeneration for re-use, sterilization, column elution, storage etc.;

4. the carrier is inexpensive to be economically acceptable. As, at the present time, no carrier material is known which satisfies all these requirements in an optimum manner, a selection will have to be made from a number of less ideal materials. Basically, all water-insoluble carrier materials are more or less suitable for the FVIII isolation process. A number of examples are mentioned below. This number is not exhaustive:

1. cross-linked agaroses;
2. cross-linked ethylenes/maleic acid anhydride (EMA) copolymers;
3. cellulose;
4. trisacryl;
5. fractogel TSK;
6. polystyrene;
7. cross-linked polyvinyl alcohol;
8. polyacrylamide;
9. silica gel;

10. cross-linked polymers based on acrylic acid as a monomer (PMMA, poly-HEMA, etc.);

11. cross-linked dextrans (Sephadex).

For the FVIII isolation illustrated in the examples, Sepharose CL 4B, Sepharose CL 2B, Sephacryl S-400, S-500, S-1000 and Fractogel TSK-HW55 were used as the carrier materials.

The ligand in the adsorbent material according to the invention is preferably the primary amino group $NH_2$, which has a relatively high pK value, so that, with a relatively high pH of 6-8, a larger fraction of the ligands is positively charged than is the case, for example, with DEAE-Sephadex, DEAE-cellulose and DMAP-EMA (Johnson). In order to realize the same charge density (adsorption capacity), a lower ligand density is thus required. As a consequence, the adsorption of the desired proteins is more specific and a purer product can be obtained. The ligand is not, however, restricted to the primary amino group. Generally speaking, all aines will be more or less suitable for the object contemplated, so that the ligands may alternatively consist of secondary, tertiary or quaternary amino groups, as shown by the examples.

The way in which the ligand is coupled to the carrier material via the spacer is not limited to one given coupling group and method either. In principle, any method is suitable by which an amino group can be immobilized via a spacer to a carrier material. Preferably, however, the coupling method satisfies the following requirements:

1. the coupling can be carried out in a simple, fast and reproducible manner;

2. a high degree of substitution (ligand density) can be obtained without the occurrence of cross-linking;

3. the reaction conditions must not of course be destructive to the matrix;

4. the resulting bond is highly stable, so that no ligand leakage will occur.

When the carrier material is a polymeric material containing free hydroxyl groups, as is the case, for example, with agaroses, a coupling can be accomplished, for example, by means of the following coupling reagents:

a. cyanohalides;
b. triazines;
c. periodate;
d. (bis-)epoxides;
e. carboxyalkyl halides;
f. divinyl sulfone;
g. tresyl and tosyl chloride;
h. carbonyl diimidazole.

One of the coupling methods most frequently used employs cyanogen bromide. It was also used to prepare the alkyl and aminoalkyl-Sepharoses mentioned above. This method does not, however, satisfy the requirements as regards degree of substitution and the absence of extra charge, and is therefore less suitable. The stability is not great either. Recently Bethell et al. (J. Biol. Chem. 254(8) (1979) 2572-2574; J.Chrom. 185(1979) 463-470; J. Chrom 218(1981) 509-518 developed a method which does appear to satisfy the requirements made. 1,1'-Carbonyldiimidazole (CDI) is used as a coupling reagent. In a first reaction step, the matrix is activated, and in a second step, for example, an amine can be coupled.

Activation takes place in an anhydrous organic solvent, such as acetone, dioxane or dimethyl formamide (DMF). The hydrogel must be transferred to it by solvent exchange. Through hydrolysis of the activated gel with sodium hydroxide, imidazole and carbon dioxide are formed, by means of which the degree of activation can be determined in a simple manner. The activated gel reacts in both organic solvent and water with amines, among other compounds, in a high yield, so that all sorts of amine-containing ligands can be coupled in a simple manner. The coupling is effectively reproducible and makes possible a high ligand density. The carbamate (urethane) bond formed is highly stable against hydrolysis and, at pH higher than 4, uncharged.

This coupling method, using CDI as the coupling reagent, and the resulting coupling group —CO—NH— are accordingly preferred in accordance with this invention.

Affinity matrices according to the invention, having the generic formula 3, can be prepared by first coupling a linear aminocarboxylic acid ester to the carrier by means of CDI activation, and then re-esterifying the ester with a diamine to form the desired gel. It is also possible for the diamine to be coupled to the free carboxylic acid group by means of the known per se carbodiimide coupling.

The ligand density of the affinity matrices according to the invention is preferably higher than 30 umoles/ml, more preferably higher than 50 umoles/ml and most preferably 60-100 umoles/ml of swollen gel. By means of the CDI activation method, a high ligand density of as high as about 200 umoles/ml can be realized easily and in a reproducible manner. A high ligand density leads to a high adsorption capacity. As a result, a lower gel/plasma ratio is possible, which ensures lower cost.

The liquid starting material which contains the coagulation factor or factors to be isolated and can be used in the process according to this invention will preferably be blood plasma, preferably fresh or freshly frozen human blood plasma. Pre-purifications and adaptations to the isolation method are not strictly necessary. The invention is not, however, limited to being used with blood plasma and, in particular, can also be applied for isolating the desired substances from (pre-purified) plasma products, such as FVIII concentrate, cryoprecipitate, and plasma first pre-treated with an anion exchanger, such as DEAE-Sephadex-A50, as described in DE-A-2,715,832, or from cell lysates, and fermentation or culture mediums obtained in a biotechnological production of FVIII or other coagulation factors.

The isolation method according to the invention, which comprises an adsorption stage and an elution stage, is preferably carried out at normal pressure and temperature, although variations are permissible. Thus, without any serious objections, the temperature can be selected within the range of from 0°-60° C., but for practical reasons room temperature is preferred. Both the adsorption stage and the elution stage can be carried out batchwise or in a column. Treatment in a column, however, is preferred especially as regards the elution stage. As regards the adsorption stage, batchwise treatment could be preferred.

As regards the period of time there are no particular restrictions either. The adsorption stage, however, will in practice take at least 10 minutes.

The affinity matrix is equilibrated by means of a buffer before use. This buffer preferably has the same pH and the same conductivity as has the liquid starting material containing the coagulation factors to be isolated. In the process according to the invention it has proved favourable for the pH to be kept at a value of 6-8, preferably about 7, during the process, and for the specific conductivity of both equilibration buffer and the liquid starting material to be less than 20 mS/cm, preferably 13-16 mS/cm. These process conditions make it possible to use blood plasma as such as the starting material, and are conducive to a relatively high yield. The process conditions, and in particular the use Of an approximately physiological pH, are also favourable for large-scale application (adjustment of the pH of large amounts of plasma to a value of 5.5 is rather difficult) and for the stability of the isolated coagulation factors, such as FVIII:C.

As regards the gel/plasma ratio, lower values are preferred in connection with lower cost and lower a specific adsorption. Indeed, the preferred gel/plasma ratio G/P used in the process according to this invention is less than ⅛, such as 1/12 to 1/30, most preferably about 1/20. Starting from plasma containing about 1 unit/ml, a G/P ratio of 1/20 means that about 20 units of coagulation factor are offered per ml gel.

The elution of the adsorbed coagulation factors is effected by increasing the conductivity of the buffer. This is preferably realized by adding sodium chloride to the buffer (e.g. up to 0.5 or 1.0M), but naturally other means can be used for this purpose, as will become apparent from the examples.

Owing to the combination of optimum process conditions and the use of plasma as the starting medium, the coagulation factors FII, FVII, FIX and FX, as well as the FVIII-vWF complex are isolated in relatively high yield and purity. Desorption of FII, FVII, FIX and FX in addition to FVIII/vWF may be undesirable if, in addition to an FVIII/vWF preparation an FVII/FIX preparation must be prepared. In addition, the presence of, in particular, FII in the desorption fraction constitutes a considerable impurity on a weight basis. Therefore, a separation between FII, FVII, FIX and FX, on the one hand and FVIII/vWF, on the other, will in some cases be desirable. This separation may, if desired, be realized in the same process stage or in a subsequent process stage. It is also possible to effect the separation before the isolation of FVIII/vWF on the materials here described. For plasma, an anion exchanger can be used for this purpose, such as DEAE-Sephadex A50. One of the examples shows this pre-treatment.

The invention is illustrated in and by the following examples.

EXAMPLES REGARDING THE PREPARATION OF ADSORBENT MATERIALS

In accordance with the experiments described below, and using different amines, derivatives of Sepharose CL 4B were prepared, which could be used as an adsorbent material (affinity matrix) for the isolation of coagulation factors, in particular from citrated human blood plasma.

Sepharose CL 4B was used in the form of a suspension in water. For the synthesis, the water must be effectively replaced by an organic solvent, such as N,N-dimethylformamide (DMF). This could be realized batchwise with relatively small quantities on a glass filter, or in a column with larger quantities. After the solvent exchange, the Sepharose matrix was activated with 1,1'-carbonyl-diimidazole (CDI) by the procedure described by Bethell (J.Biol.Chem. 254 (1979), 2572-2574).

Thereafter an amino-alkanoic acid can be coupled with the activated gel to produce a carboxyalkyl-Sepharose as an intermediate. An active N-hydroxysuccinimide (NHS) ester can be obtained by carbodiimide coupling, using, e.g., 1-ethyl-3-(3-dimethylaminopropyl)carbodiimide.HCl (EDAC). This active ester reacts readily with an alkane diamine, whereby the desired aminoalkyl-carbamylalkylSepharose can be obtained in a quantitative yield either in a separate or the same reaction stage.

As all Sepharose derivatives contain basic amino groups as ligands, the ligand density can be simply determined by acid-base titration or by nitrogen elemental analysis.

The solvent exchange, whereby water is replaced by dimethylformamide or any other organic solvent, was carried out in two different ways, depending on the amount of hydrogel used:

1. Generally speaking, 12 ml gel suspension (10 ml moist cake) was washed three times on a glass filter (G3) with distilled water and sucked to substantial dryness, and successively washed once with distilled water/DMF 70:30 (v/v), once with 30:70 and thrice with DMF. This procedure turned out to be effective for the replacement of water in small amounts of hydrogel.

2. In other cases, up to 400 ml of the gel (480 ml suspension) was poured into a glass column (26×750 mm), and the column was washed with two column volumes of distilled water. Thereafter, a linear water/DMF gradient (400 ml) of 0-100% DMF was applied to replace the water, and finally the gel was washed with about 1 volume of DMF until the effluent was completely free from water (which was checked by water analysis of the effluent).

CDI activation was carried out by suspending the gel in an equal amount of DMF (v/v) and adding a known quantity of CDI, based on the original gel volume in water (e.g. 0.1 mmole/ml gel). The suspension was carefully stirred or shaken at room temperature for at least 20 min., and the activated gel was washed three times on a glass filter with the same quantity of DMF.

Amine coupling was carried out in the organic solvent (DMF, dioxane, acetone) or in aqueous solution, depending upon the solubility of the amine and the properties of the gel to be obtained. For this purpose a known quantity (generally at least five times the desired total ligand density TLD)) of the amine was dissolved in one volume of the solvent and then added to the same volume of activated gel, followed by stirring or shaking carefully at room temperature for the desired period of time.

Amines containing a carboxyl group were dissolved in distilled water and sodium hydroxide granules were added to the solution until the pH was about 12.6. In cases in which the carboxyl group was esterified, the ester was dissolved in DMF (5 ml/g) and an equimolar quantity of triethyl amine (TEA) was dropped into the stirred solution to neutralize the hydrogen chloride. The triethyl amine.HCl was precipitated and removed by filtration.

For the coupling of amines to NHS-gels (see the following description of the carbodiimide coupling) in aqueous solution, a 0.1M sodium hydrogen carbonate buffer with a pH of 8.4, and containing 0.5M sodium chloride, was used as the solvent. The coupling period was 150 min.

To remove excess amine after the coupling, the gel was washed with the solvent, 0.1N hydrochloric acid, 0.1N sodium hydroxide, and distilled water, depending on the coupled amine (with or without carboxyl group)

and the specific application (further activation, titration, tests).

After coupling an n-amino-alkane carboxyiic acid-ethylester to a CDI-activated gel, the free acid could be obtained by hydrolysis of the ethyl ester. For this purpose the gel was sucked to dryness and suspended in twice the original gel volume of 0.5N sodium hydroxide. The suspension was incubated end over end at room temperature for 6 hours, whereafter the gel was washed on a glass filter with 1N sodium hydroxide and twice with distilled water. Subsequently, the carboxy gel was titrated to determine the ligand density (LD).

The carbodiimide coupling was carried out by suspending the carboxyl group containing gel in an equal volume of solvent, which solvent may be distilled water, DMF/dioxane 80:20 (v/v) or DMF. In some cases, it was necessary to carry out solvent exchange. N-hydroxysuccinimide NHS) and 1-ethyl-3-(3-dimethylamino-propyl) carbodiimide (EDAC) were added, and the suspension was shaken at room temperature for 18–22 hours. Generally speaking, the amount of NHS was 6–10 times and the amount of EDAC 4–8 times the total ligand density of the carboxy gel.

Where water was used as the solvent, 0.1N hydrochloric acid was added until the pH was 4.1, and this pH was kept constant for 30 minutes.

After the reaction, the gel was washed three times on a glass filter (G3) with the solvent (DMF or water containing 1 mM HCl) to remove the excess of NHS and EDAC, whereafter the NHS gel was ready for amine coupling.

The hydrogels were kept at 4° C. in phosphate-buffered saline (PBS) containing 0.01% thimerosal, or also sometimes in adsorption buffer instead of PBS.

The titration was normally carried out with 4–8 ml of the hydrogel. The gel volume was determined after 10 minutes' centrifugation at 1500×g and 30 minutes waiting time. The gel was equilibrated with 0.05N sodium hydroxide by washing it three times with it, was sucked to dryness on a glass filter, suspended in 50 ml distilled water, and stirred. Thereafter, 0.100N hydrochloric acid was added at a rate of 0.125 ml/min., and pH and conductivity were measured and recorded. The ion exchange capacity (for charged ligands this is equal to the total ligand density (TLD)), could be calculated from the curve of the conductivity (which clearly shows the starting point and the end of the titration) and the gel volume; the apparent pK-value was obtained from the pH curve halfway through the titration at a conductivity of 5 mS/cm. For a known gel volume, the ligand density (LD) can be calculated.

The gel volume (GV) of the gel derivatives was normally determined in PBS, unless otherwise indicated. In a 15 ml polystyrene tube with a ml graduation, about 7 ml gel suspension was centrifuged for 10 minutes at 2000 rpm. Thereafter, the precipitated gel was allowed to stand at room temperature for at least 15 minutes, and the volume (±0.2 ml) is read. When the gel is in an organic solvent (such as DMF), normally the original volume in an aqueous solution is given.

Aminoalkyl-carbamylalkyl-Sepharoses with different chain lengths

Example 1

In the cases where aminoalkanoic acids were coupled with CDI-activated Sepharose (CDI-SEPH) after solvent exchange with water, the coupling effectiveness was relatively low (10–20%), probably as a result of hydrolysis of the activated group. For this reason, ethyl esters of aminoalkanoic acids (C1-3) were coupled with one-third of a lot of 100 ml CDI activated Sepharose (10 mmoles CDI; Activation Reaction Time ART =90 minutes) in DMF (Coupling Reaction Time CRT=20 hours; CDI/amine=1/7) and hydrolyzed to produce the carboxy gels. The results are shown in the following Table 1.

TABLE 1

| | Coupling of esterified aminoalkanoic acids to CDI-Sepharose | | | | |
|---|---|---|---|---|---|
| Gel Code | TLD mmoles | YIELD % | GV ml | LD umoles/ml | pK |
| C1-SEPH.22.05.86 | 1.51 | 46 | 35 | 43 | 5.0 |
| C2-SEPH.22.05.86 | 1.91 | 58 | 33 | 58 | 5.4 |
| C3-SEPH.22.05.86 | 1.60 | 48 | 32 | 50 | 5.6 |

From the three carboxy gels (Cm-CDI-SEPH 22.05.86), nine aminoalkyl-carbamylalkyl-Sepharoses (An-Cm-CDI-SEPH) were prepared by activation with NHS and EDAC and coupling of an n-alkane diamine (n=2,3,4) in DMF (CRT=16 hours) with one-third of each carboxy gel. The gels were used for column-wise adsorption tests. Data about the synthesis are set forth in the following Table 2.

TABLE 2

| | Synthesis of aminoalkyl-carbamylalkyl-Sepharoses. | | | | |
|---|---|---|---|---|---|
| Gel Code | TLD umoles | Yield % | GV ml | LD umoles/ml | pK |
| A2-C1.29.05.86 | 225 | 45 | 9.0 | 25 | 8.8 |
| A3-C1.29.05.86 | 260 | 52 | 10.0 | 26 | 9.1 |
| A4-C1.29.05.86 | 223 | 45 | 9.3 | 24 | 9.3 |
| A2-C2-28.05.86 | 336 | 53 | 7.3 | 46 | 8.7 |
| A3-C2-28.05.86 | 367 | 58 | 7.8 | 47 | 8.9 |
| A4-C2-28.05.86 | 308 | 48 | 7.5 | 41 | 8.7 |
| A2-C3-28.05.86 | 292 | 55 | 7.3 | 40 | 8.5 |
| A3-C3-28.05.86 | 310 | 58 | 7.2 | 43 | 8.9 |
| A4-C3-28.05.86 | 301 | 56 | 7.0 | 43 | 8.7 |

Example 2

To study the effect of chain length and composition on the batchwise adsorption and columnwise elution, 5 series of aminoalkyl-carbamylalkyl-Sepharoses (An-Cm-CDI-SEPH) were prepared. Either the esterified aminoalkanoic acid in DMF (for C1-3) or the free aminoalkanoic acid in a small quantity of water (for C4-5) were coupled to CDI-SEPH, which in both cases was suspended in DMF (ART=90 minutes; CRT=16 hours). The data of this synthesis are set forth in the following Table 3.

TABLE 3

| | Synthesis of carboxyalkyl-Sepharoses with different chain lengths | | | | | | |
|---|---|---|---|---|---|---|---|
| Gel Code | SEPH. VOL ml | CDI umoles | AMINE mmoles | TLD mmoles | YIELD % | GV ml | LD umoles/ml |
| C1-SEPH.22.08.86 | 100 | 10 | 90 | 3.1 | 31 | 72 | 43 |
| C2-SEPH.05.08.86 | 100 | 10 | 60 | 4.2 | 42 | 70 | 60 |

TABLE 3-continued

Synthesis of carboxyalkyl-Sepharoses with different chain lengths

| Gel Code | SEPH. VOL ml | CDI umoles | AMINE mmoles | TLD mmoles | YIELD % | GV ml | LD umoles/ml |
|---|---|---|---|---|---|---|---|
| C3-SEPH.22.08.86 | 100 | 10 | 60 | 3.9 | 39 | 70 | 55 |
| C4-SEPH.22.08.86 | 100 | 20 | 40 | 5.0 | 25 | 70 | 72 |
| C5-SEPH.29.01.87 | 740 | 96 | 640 | 62.0 | 65 | 667 | 93 |
| C4-SEPH.28.01.87 | 200 | 26 | 170 | 13.7 | 53 | 180 | 76 |

Suspensions of the carboxy gels (Cm-CDI-SEPH) in DMF were activated with NHS and EDAC and divided into 10 equal portions (GV=7.0 ml, except for C5-SEPH 29.01.87), for coupling with an excess of the n-alkane diamines (CRT=16 hours; LD/amine=1/100). The results are set forth in Tables 4–8.

TABLE 4

Synthesis of aminoalkyl-carbamylmethyl-Sepharoses with different chain lengths.

| Gel Code | TLD umoles | Yield % | GV ml | LD umoles/ml |
|---|---|---|---|---|
| A2-C1-10.09.86 | 186 | 60 | 4.7 | 40 |
| A3-C1-10.09.86 | 199 | 64 | 4.9 | 41 |
| DMA3-C1-10.09.86 | 198 | 64 | 5.2 | 39 |
| A4-C1-10.09.86 | 149 | 48 | 4.2 | 36 |
| A5-C1-10.09.86 | 180 | 58 | 4.7 | 38 |
| A6-C1-10.09.86 | 188 | 61 | 6.0 | 31 |
| A7-C1-10.09.86 | 204 | 66 | 6.1 | 34 |
| A8-C1-10.09.86 | 191 | 62 | 6.6 | 29 |
| A9-C1-10.09.86 | 206 | 66 | 7.3 | 28 |

TABLE 5

Synthesis of aminoalkyl-carbamylethyl-Sepharoses with different chain lengths

| Gel Code | TLD umoles | YIELD % | GV ml | LD umoles/ml |
|---|---|---|---|---|
| A2-C2-11.08.86 | 371 | 88 | 6.5 | 57 |
| A3-C2-11.08.86 | 359 | 85 | 6.3 | 57 |
| DMA3-C2-11.08.86 | 472 | 100 | 7.5 | 63 |
| A4-C2-11.08.86 | 321 | 76 | 6.3 | 51 |
| A5-C2-11.08.86 | 282 | 67 | 6.0 | 47 |
| A6-C2-11.08.86 | 260 | 62 | 5.3 | 49 |
| A7-C2-11.08.86 | 237 | 56 | 5.5 | 43 |
| A8-C2-11.08.86 | 256 | 61 | 6.4 | 40 |
| A9-C2-11.08.86 | 196 | 47 | 5.6 | 35 |

The gels were prepared from C2-CDI-SEPH.05.08.86 (TLD = 4.2 mmoles)

TABLE 6

Synthesis of aminoalkyl-carbamylpropyl-Sepharoses with different chain lengths

| Gel Code | TLD umoles | YIELD % | GV ml | LD umoles/ml |
|---|---|---|---|---|
| A2-C3.10.09.86 | 314 | 81 | 6.5 | 48 |
| A3-C3.10.09.86 | 256 | 66 | 5.4 | 48 |
| DMA3-C3.10.09.86 | 334 | 86 | 6.2 | 54 |
| A4-C3.10.09.86 | 262 | 67 | 5.5 | 48 |
| A5-C3.10.09.86 | 251 | 64 | 5.8 | 43 |
| A6-C3.10.09.86 | 250 | 64 | 5.5 | 46 |
| A7-C3.10.09.86 | 306 | 78 | 5.2 | 60 |
| A8-C3.10.09.86 | 187 | 48 | 5.3 | 36 |
| A9-C3.10.09.86 | 219 | 56 | 6.3 | 35 |

The gels were prepared from C3-CDI-SEPH.22.08.86 (TLD = 3.9 mmoles)

TABLE 7

Synthesis of aminoalkyl-carbamylbutyl-Sepharoses with different chain lengths.

| Gel Code | TLD umoles | YIELD % | GV ml | LD umoles/ml |
|---|---|---|---|---|
| A2-C4.10.09.86 | 302 | 60 | 4.9 | 62 |
| A3-C4.10.09.86 | 277 | 55 | 4.6 | 60 |
| DMA3-C4.10.09.86 | 372 | 74 | 5.2 | 72 |
| A4-C4.10.09.86 | 382 | 76 | 5.7 | 67 |
| A5-C4.10.09.86 | 269 | 54 | 4.3 | 63 |
| A6-C4.10.09.86 | 302 | 60 | 5.4 | 56 |
| A7-C4.10.09.86 | 450 | 90 | 6.8 | 66 |
| A8-C4.10.09.86 | 257 | 51 | 5.7 | 45 |
| A9-C4.10.09.86 | 242 | 48 | 3.8 | 65 |
| A4-C4-03.02.87 | 7168 | 59 | 128 | 56 |

The gels were prepared from C4-CDI-SEPH.22.08.86

TABLE 8

Synthesis of aminoalkyl-carbamulpentyl-Sepharoses with different chain lengths

| Gel Code | C5-SEPH ml | TLD mmoles | YIELD % | GV ml | LD umoles/ml |
|---|---|---|---|---|---|
| A2-C5.03.02.87 | 10.3 | 0.82 | 86 | 9.8 | 84 |
| A3-C5.03.02.87 | 10.9 | 0.75 | 74 | 10.4 | 72 |
| DMA3-C5.03.02.87 | 60 | 6.86 | 100 | 75.4 | 91 |
| A4-C5.03.02.87 | 400 | 17.05 | 46 | 341 | 50 |
| A5-C5.03.02.87 | 10.3 | 0.59 | 62 | 9.0 | 66 |
| A6-C5.03.02.87 | 60 | 4.31 | 77 | 68.4 | 63 |
| A7-C5.03.02.87 | 11.6 | 0.61 | 56 | 10.3 | 59 |

The gels were prepared from C5-CDI-SEPH.29.01.87

TABLE 9

Average values and standard deviations from nine experiments of ligand density, yield and volume for synthesized aminoalkyl-carbamylalkyl-Sepharoses from 9 experiments.

| Gel Code | TLD umoles | YIELD % | GV ml | LD umoles/ml |
|---|---|---|---|---|
| An-C1.10.09.86 | 189 ± 16 | 61 ± 5 | 5.5 ± 0.9 | 35 ± 5 |
| An-C2.11.08.86 | 306 ± 80 | 71 ± 16 | 6.2 ± 0.6 | 49 ± 8 |
| An-C3.10.09.86 | 264 ± 44 | 68 ± 11 | 5.7 ± 0.5 | 46 ± 7 |
| An-C4.10.09.86 | 317 ± 65 | 63 ± 13 | 5.2 ± 0.8 | 62 ± 7 |

Carrier materials other than Sepharose CL-4B were provided with aminoalkyl-carbamylalkyl side chains and tested in a similar manner (see Example 6).

The gel codes specify the nature of the gel and its date of preparation. The gels synthesized and examined all satisfied the generic formula (3):

Sepharose—O—CO—NH—(CH$_2$)$_m$—CO—N-
H—(CH$_2$)$_n$—NR$^1$R$^2$.

The number following the letter A in the gel codes indicates the value of n, the number following the letter C indicates the value of m. The gel A2-C3-28.05.85, for example, satisfies the formula
Sepharose—O—CO—NH—(CH$_2$)$_3$—CO—N-
H—(CH$_2$)$_2$—NH$_2$, and was prepared on May 28, 1986.

The abbreviation DMA3 means the group N,N-dimethylaminopropyl.

Examples with regard to the Factor VIII isolation

Purification of solidification factors

In the experiments described below, an adsorbent material (also referred to as affinity matrix or gel) was used, which was equilibrated, and suspended in, adsorption buffer. Thereafter, in simple adsorption experiments, the gel and a normal plasma pool (NPP) were incubated either columnwise or batchwise at different gel/plasma ratios under specific conditions.

Gels exhibiting a high Factor VIII adsorption (exceeding 75% at a G/P ratio of 1:8) were re-incubated and then eluted columnwise with 1M sodium chloride in buffer. The Factor VIII content in the eluate and the total protein concentration were determined, taking the normal plasma pool as a reference. From these data the Factor VIII recovery and purification factor (PUR) could be obtained with facility. In case a standard was used as a reference (for FVIII:C the CLB-PS41 and for the protein human serum albumin), the specific activity could be determined (Table 12).

For gels with promising results, the recovery and specific activity in the eluate of Factors II, VII, IX and X were also determined, because these coagulation factors can also be adsorbed to the gel and be eluted.

The normal plasma pool (NPP) was obtained by combining freshly citrated plasma (CPDA-1 plasma) from at least 15 donors (human serum albumin HSA=39.6±1.0 mg/ml; IgG=11.8±0.4 mg/ml). If necessary, the pH was adjusted to 7.4 with 1N acetic acid prior to freezing. In the case of pH 5.5, acetic acid was added to the plasma shortly before use to obtain the desired pH.

Batchwise Adsorption

The hydrogel to be tested was equilibrated on a glass filter with a 0.1M acetate/lysine buffer at a desired pH, and suspended in 1.2 times the gel volume. A known quantity of this suspension was incubated in a plastics tube end over end with human plasma (NPP) at the same pH and at room temperature for 5–120 minutes.

The 0.1M acetate/lysine buffer used contained, per liter, 8.20 g sodium acetate, 18.27 g L-lysine monohydrochloride, 2.94 g trisodium citrate, 1.0 ml calcium chloride solution of 1.0M, and 1N sodium hydroxide or 1N hydrochloric acid to adjust the pH.

In order to obtain an impression of the effect of the pH on the FVIII:C adsorption, an incubation was carried out at a pH of between 7.4 and 5.5. To adjust the pH of plasma and buffer, 1.0M acetic acid was added slowly.

After incubation, the mixture was centrifuged at full speed for 2 minutes, and the supernatant plasma (SUP) was generally stored on ice for Factor VIII determination.

When elution was necessary, the hydrogel was poured into a column (Pharmacia C10/10) and eluted in the manner described hereinafter. During washing, the buffer was collected in the supernatant plasma. It was assumed that this fraction contained the non-bonded proteins (non-adsorbed protein fraction NADS).

Columnwise Adsorption

For columnwise adsorption, about 5 ml of the hydrogel was used. The gel was poured into a column (Pharmacia C10/10) and equilibrated with the 0.1M acetate/lysine buffer at pH 7.0 or 5.5. A known quantity (1–30 ml) of human plasma (NPP) with the same pH and the same conductivity as the buffer was applied to the column at room temperature, while 1–5 ml NPP was stored on ice during the experiment (REF). The flow rate was kept constant at 0.3–1.0 ml/min. by means of a peristaltic pump (Pharmacia P-1). The UV adsorption at 280 nm was monitored in the column eluate by means of a Pharmacia Single Path Monitor IV-1. As soon as protein was eluted from the column (after 2–3 ml, depending on the hydrogel) the eluate was collected up to a certain volume (plasma +washing buffer) (NADS) and stored on ice.

Columnwise Elution

The columnwise elution began after washing with buffer (normally 10–20 ml) until no protein could be detected any longer. Elution of the bonded protein was then effected with the same buffer containing 1.0M sodium chloride. The eluate in which protein was detected (about 10 ml) was collected and stored on ice (the eluted protein fraction ELU).

To correct the high sodium chloride concentration for FVIII:C APTT determination (the activated partial thromboplastin time) the ELU was appropriately diluted with APTT buffer containing less sodium chloride.

Protein concentrations were determined with the Bradford Protein Assay, BioRad (BPA), based on the shift of the adsorption maximum of Coomassie Brilliant Blue G-250 when bonding to proteins occurs, or were determined with the BCA Protein Assay, Pierce (BCA) at 60° C., which is based on the biuret reaction, using in both cases the conditions described by the producer. Duplicate samples were appropriately diluted and analyzed, in accordance with producer's instructions, against a standard curve of normal plasma (the BCA test gave slightly higher values for the same samples than did the BPA test) or human serum albumin (54.1 ml/ml).

The antigen concentrations (FVIII:Ag and vWF:Ag) were determined by means of an Enzyme Linked Immuno Sorbent Assay (ELISA), based on the monoclonal antibodies CLB-CAg A and CLB-CAg 117 for FVIII:Ag and CLB-RAg 20 and CLB-RAg 35 for vWF:Ag. The abbreviations used have the following meanings:

FVIII=the blood coagulation factor VIII;
vWF=the von Willebrand factor, sometimes designated in the literature as FVIIIR;
FVIII:C=the coagulation activity of Factor VIII;
FVIII:Ag=factor VIII antigen; and
vWF:Ag=Von Willebrand factor antigen, sometimes designated in the literature as FVIIIR:Ag.

The coagulation factor activities were determined with a one-stage APTT test as described by Hardisty and McPherson, Thromb.Diath.Haemorr. 7 (1962), 215–229. The assay was carried out on a LODE LC 6 Coagulatometer with a synthetic substrate for FII and FX, congenitally deficient substrate for FVII and FVIII, and immunodepleted substrate for FIX. The reference was prepared by serial dilution (1/10 to 1/320) of a normal plasma standard.

The FVIII Coatest for the measurement of FVIII:C activity on a chromogenic substrate was carried out in accordance with producer's instructions (Kabi Vitrum). The results were well consistent with the FVIII:C APTT. Serial dilutions (1/160 to 1/800) of normal plasma (CLB-PS41, FVIII:C=0,78 U/ml) were taken as a reference.

Albumin and immunoglobulin G were measured with a nephelometric method. Fibrinogen (Fb) and fibronectin (Fn) were determined by radial immunodiffusion according to Mancini.

Example 3

Batchwise Adsorption Experiments

To gain information about the adsorption of FVIII:C under different conditions, small-scale batchwise adsorption experiments were conducted with virtually all synthesized gels. About 1 ml plasma was incubated with gel at a given gel/plasma ratio (pH=7.4; AT=30 min.), and the supernatant plasma (SUP) was diluted 1:10 and analyzed in duplicate for FVIII:C with APTT; this was compared with the same test, carried out with the matrix starting material (Sepharose CL 4B). The results are not shown.

Example 4

Columnwise Adsorption Experiments

Effect of alkyl chain length on adsorption and elution

To study the effect of the total chain length on the FVIII adsorption during columnwise adsorption, three series of aminoalkyl-carbamylalkyl-Sepharoses (LD=25±1, 45±3 and 42±2 umoles/mil) were tested. Plasma (4 ml NPP) was applied to the column (5 ml; G/P=1.25; flow rate FR=0.3 ml/min.; pH 7.4), the column was washed with buffer (NADS=20 ml) and eluted with 1.0M sodium chloride (ELU=8 ml). The results of the FVIII:C, FVIII:Ag and vWF:Ag analysis are shown in the following Table 10. Data with regard to the protein adsorption are not given, because these were too low to be determined. At the same time, a columnwise elution was carried out. The results regarding FVIII, vWF and protein are also given in Table 10.

TABLE 10

Column adsorption and column elution on aminoalkyl-carbamylalkyl-Sepharose with different chain lengths.

| Gel Code | % FVIII:C ADS | % FVIII:C ELU | % FVIII:Ag ADS | % FVIII:Ag ELU | % vWF:Ag ADS | % vWF:Ag ELU | % Protein ELU | Purification factor |
|---|---|---|---|---|---|---|---|---|
| A2-C1-29.05.86 | 15 | 4 | 0 | 5 | 0 | 2 | 0.15 | 26 |
| A3-C1-29.05.86 | 4 | 6 | 7 | 10 | 5 | 3 | 0.33 | 18 |
| A4-C1-29.05.86 | 19 | 9 | — | 4 | 11 | 4 | 0.50 | 18 |
| A2-C2-28.05.86 | 19 | 19 | 17 | 13 | 9 | 5 | 0.76 | 25 |
| A3-C2-28.05.86 | 63 | 39 | 65 | — | 54 | 20 | 0.75 | 52 |
| A4-C2-28.05.86 | 57 | 52 | 60 | — | 41 | 22 | 0.58 | 90 |
| A2-C3-28.05.86 | 30 | 16 | 36 | 80 | 32 | 10 | 0.80 | 20 |
| A3-C3-28.05.86 | 95 | 55 | 95 | — | 93 | 26 | 0.93 | 59 |
| A4-C3-28.05.86 | 98 | 50 | 93 | — | 93 | 31 | 0.94 | 53 |

After een preceding investigation of FVIII interaction during columnwise adsorption and elution with three series of aminoalkyl-carbamylalkyl-Sepharose, five larger series with different chain length were prepared. The tests were carried out at pH 7.4 during batchwise adsorption and columnwise elution for only those gels which exhibited relatively high adsorption capacities for FVIII. The gel was incubated with plasma (12 ml NPP; pH 7.4; G/P=0.10; adsorption time AT=30 min.), washed with buffer (FR=1.0 ml/min; NADS=50 ml) and eluted with 1.0M sodium chloride (FR=0.5 ml/min.; ELU=20 ml). Eluted FVIII (APTT) and vWF were analyzed in duplicate at three dilutions. The data are set forth in the following Table 11.

TABLE 11

Batchwise adsorption and columnwise elution on aminoalkyl-carbamylalkyl-Sepharoses.

| Gel Code | % FVIII:C SUP | % FVIII:C ADS | % FVIII:C ELU/ADS | % FVIII:C ELU | % Protein* ELU | Purification factor |
|---|---|---|---|---|---|---|
| A4-C2-11.08.86 | — | 85 | 64 | 54 | 0.27 | 200 |
| A5-C2-11.08.86 | 75 | 75 | 37 | 28 | 0.14 | 200 |
| A6-C2-11.08.86 | 96 | 98 | 45 | 44 | 0.21 | 210 |
| A7-C2-11.08.86 | 97 | 98 | 21 | 21 | 0.29 | 72 |
| A5-C3.10.09.86 | 53 | 70 | 37 | 26 | 0.11 | 236 |
| A6-C3.10.09.86 | 80 | 92 | 28 | 26 | 0.15 | 173 |
| A7-C3.10.09.86 | 98 | 99 | 14 | 14 | 0.23 | 61 |
| A3-C4.10.09.86 | 95 | 98 | 57 | 56 | 0.38 | 147 |
| A4-C4.10.09.86 | 95 | 98 | 60 | 60 | 0.35 | 171 |
| A4-C4.10.09 86** | 78 | 90 | 67 | 64 | 0.33 | 194 |
| A5-C4.10.09.86 | 98 | 99 | 44 | 44 | 0.33 | 133 |
| A6-C4.10.09.86 | 98 | 100 | 40 | 40 | 0.54 | 74 |
| DMA3-C5.03.02.87 | — | 95 | 65 | 62 | 0.50 | 124 |
| A4-C5.03.02.87 | — | 96 | 57 | 55 | 0.56 | 98 |

TABLE 11-continued

Batchwise adsorption and columnwise elution on amino-alkyl-carbamylalkyl-Sepharoses.

| Gel Code | % FVIII:C | | | | % Protein* | Purification |
| | SUP | ADS | ELU/ADS | ELU | ELU | factor |
|---|---|---|---|---|---|---|
| A6-C5.03.02.87 | — | 96 | 43 | 41 | 1.08 | 38 |

*determined with BPA
**this experiment was carried out at G/P = 0.05.

As can be calculated from Table 11, the relative elution (ELU/ADS) is related to the alkyl chain length n of the aminoalkyl group (ELU/ADS=62±4, 39±3, 39±9 and 18±4 for n=4, 5, 6 and 7, respectively). No such direct relationship could be concluded for the alkyl chain length m (ELU/ADS=42±15, 26±9, 54±10 and 55±9 for m=2, 3, 4 and 5, respectively).

gel. The mean values and standard deviation for FVIII and total protein are shown in the following Table 12.

TABLE 12

Batchwise adsorption and columnwise elution of 20 ml NPP on 2 ml affinity gel: FVIII and total protein; n = number of experiments.

| Gel Code | LD | NPP U/ml | % FVIII:C ADS | ELU | YIELD U/kg NPP | % PROTEIN* ELU | FVII:C E/mg |
|---|---|---|---|---|---|---|---|
| A4-C4-03.02.87 | 54 | 0.97 | 93 ± 2 | 55 ± 9 | 530 ± 18 | 0.28 | 1.97 ± .14 |
| DMA3-C5-03.02.87 | 91 | 0.99 | 95 ± 2 | 62 ± 16 | 620 ± 25 | 0.50 | 1.21 ± .17 |
| A4-C5-03.02.87 | 54 | 0.94 | 96 ± 1 | 55 ± 5 | 500 ± 16 | 0.56 | 0.98 ± .12 |
| A6-C5-03.02.87 | 63 | 0.90 | 96 ± 1 | 41 ± 15 | 360 ± 6 | 1.08 | 0.29 ± .13 |

*determined with BCA

The following Tables 13 and 14 show the result of the assay of coagulation factors and other proteins for the same experiments. The values for albumin and immunoglobulin G in the eluate were below the detection threshold (<0.03%).

TABLE 13

Batchwise adsorption and columnwise elution of 20 ml NPP on 2 ml affinity gel: coagulation factors FII, FVII, FIX and FX

| Gel Code | % FII:C ADS | ELU | % FVII:C ADS | ELU | % FIX:C ADS | ELU | % FX:C ADS | ELU | FIX E/mg |
|---|---|---|---|---|---|---|---|---|---|
| A4-C4-03.02.87 | 91 | 56 | 39 | 7 | 97 | 51 | 91 | 56 | 1.64 |
| DMA3-C5-03.02.87 | 98 | 56 | 60 | 40 | 100 | 67 | 98 | 67 | 1.13 |
| A4-C5-03.02.87 | 97 | 67 | 66 | 80 | 99 | 67 | 97 | 89 | 1.11 |
| A6-C5-03.02.87 | 99 | 67 | 91 | 100 | 100 | 67 | 99 | 78 | 0.49 |

TABLE 14

Batchwise adsorption and columnwise elution of 20 ml NPP 2 ml affinity gel: vWF, FVIII:Ag, fibrinogen and fibronectin

| Gel Code | % vWF:Ag ADS | ELU | Desorption fraction FVII:C/Ag | FVIII:C/vWF:Ag | % Fb:Ag ADS | ELU | % Fn:Ag ADS | ELU |
|---|---|---|---|---|---|---|---|---|
| A4-C4-03.02.87 | 94 | 46 | 1.02 | 1.14 | 5 | 0 | 11 | <4 |
| DMA3-C5-03.02.87 | 97 | 56 | 0.61 | 1.38 | 11 | 1 | 6 | <4 |
| A4-C5-03.02.87 | 99 | 46 | 0.92 | 1.17 | 1 | 2 | 40 | 31 |
| A6-C5-03.02.87 | 99 | 19 | 1.00 | 2.65 | 14 | 16 | 96 | 69 |

Example 5

Reproducibility with Promising Matrices

To examine the reproducibility of the affinity chromatography method, a series of four promising hydrogels was used for batchwise adsorption and columnwise elution experiments. Plasma (20 ml NPP) was incubated with gel (G/P=0.1; AT=45 min.; pH is 7.4), washed with buffer (FR=1.0 ml/min.; NADS=32 ml) and eluted with 1.0M sodium chloride (FR=0.5 ml/min.; ELU=20 ml). FVIII:C in NPP, NADS and ELU was determined using the FVIII Coatest against a plasma standard. The experiment was repeated n times for each Example 6

Isolation of FVIII/vWF on Carrier Materials Other Than Sepharose CL-4B

Using the procedure as described above, carrier materials other than Sepharose CL-4B were provided with aminoalkyl-carbamylalkyl ligand-spacer combinations. These materials were contacted with plasma in a manner as described in Example 5. The results of the isolation of FVIII/vWF on aminobutyl-carbamylbutyl, coupled to various carrier materials, are set forth in the following

TABLE 15

Batchwise adsorption and columnwise desorption of 20 ml normal plasma on 2 ml A4-C4 affinity matrix with different carrier materials: FVIII:C, vWF:Ag and total protein.

| carrier material | LD (umoles/ml) | FVIII:C (%) ADS | FVIII:C (%) DES | vWF:Ag (%) ADS | vWF:Ag (%) DES | Protein (%) DES |
|---|---|---|---|---|---|---|
| Sepharose CL 4B | 54 | 93 | 55 | 94 | 46 | 0.44 |
| Sepharose CL 2B | 50 | 70 | 70 | nd* | nd | 0.42 |
| Sephacryl S400 | 60 | 97 | 53 | 92 | 53 | 0.53 |
| Sephacryl S500 | 68 | 84 | 65 | 49 | 33 | 0.49 |
| Sephacryl S1000 | 44 | 96 | 85 | nd | nd | 0.56 |
| Fractogel TSK HW55 | 150 | 92 | 90 | 53 | 30 | 0.46 |

*nd means: not determined, also in the following Tables.

Example 7

Isolation of FVIII/vWF from Other Sources: Cryoprecipitate 10 ml large-pool cryoprecipitate (22 U FVIII:C and 49 mg protein per ml, obtained from the CLB in Amsterdam) was mixed for 45 minutes with 8 ml affinity matrix of the DMA3-C5-Sepharose CL-4B.03.02.87 type. The following Table 16 shows the results of adsorption and desorption (columnwise using different buffers) with regard to FVIII, vWF and total protein.

TABLE 16

Batchwise adsorption of 10 ml large-pool cryoprecipitate on 8 ml affinity matrix DMA3-C5-Separose CL-4B. 03.02.87, followed by columnwise desorption using different buffer compositions. FVIII:C, vWF:Ag and total protein (averages of 2 experiments).

| desorption buffer composition | FVIII:C (%) ADS | FVIII:C (%) DES | vWF:Ag (%) ADS | vWF:Ag (%) DES | FVIII:C U/mg protein |
|---|---|---|---|---|---|
| 0.125 M CaCl$_2$ | 72 | 39 | 12 | 5.5 | 2.7 |
| 0.125 M CaCl$_2$ + 1 M glucose | 72 | 42 | 28 | 3.3 | 3.3 |
| 0.125 M CaCl$_2$ + 0.2% Tween 80 | 72 | 58 | 52 | nd | nd |
| 0.5 M NaCl | 88 | 37 | 31 | 5.2 | 2.2 |
| 0.5 M NaCl + 1% Tween 80 | 82 | 53 | 42 | nd | nd |
| 1.0 M NaCl + 1% Tween 80 | 82 | 50 | 42 | nd | nd |

Example 8

Isolation of FVIII/vWF from Other Sources: Plasma Pretreated with DEAE-Sephadex A 50

By using the anion exchanger DEAE-Sephadex A 50 (Pharmacia, Uppsala, Sweden), it is possible to selectively isolate coagulation factors II, VII, IX and X from plasma without FVIII/vWF being bonded to any appreciable extent. In addition to the separation between FII, FVII, FIX and FX, on the one hand, and FVIII/vWF, on the other, the pre-treatment has two additional advantages for the isolation of FVIII/vWF by means of the affinity matrices described: higher capacity (because more binding places are available for FVIII/vWF adsorption) and superior purity (because, in particular, FII is not present in the isolated FVIII/vWF as a contamination).

Pre-treatment of Plasma with DEAE-Sephadex A 50, Followed by Isolation of FVIII/vWF on Affinity Matrices Freshly deep-frozen plasma (10–20 donors, obtained from the CLB in Amsterdam) was quickly defrosted. After the temperature of the plasma had been raised to 15° C., DEAE-Sephadex A 50 (Pharmacia, Sweden), swollen in 150 mM NaCl, was added to the plasma in a ratio of 0.5 g dry Sephadex per 1 of plasma. The suspension was stirred for 45–60 minutes, whereafter the plasma was separated from the DEAE-Sephadex by means of a 20 μm nylon gauze. The DEAE-Sephadex was then transferred to a column and washed with 180 mM NaCl in 10 mM trisodium citrate, pH 7 and eluted with 2000 mM NaCl in 10 mM trisodium citrate, pH 7. The filtrate obtained after DEAE-Sephadex A 50 treatment was contacted with various affinity matrices in various ratios. Table 17 shows the results of a number of pre-treatments of plasma with DEAE-Sephadex. The result of the desorption of the DEAE-Sephadex is also shown. Table 18 shows the results of a number of experiments in which pre-treated plasma was contacted with various affinity matrices.

TABLE 17

Pre-treatment plasma (3-8 1) with DEAE-Sephadex A 50 (0.5 g/l plasma) by batchwise incubation for 45-60 min. (15° C.). Columnwise desorption (2M NaCl). FII, FVII, FVIII:C, FIX, FX and total protein (average values of 6 experiments).

| | content in pool (U/ml) | adsorption (%) | desorption (%) |
|---|---|---|---|
| FII | 0.90 | 90 | 55 |
| FVII | 1.01 | 10 | 8 |
| FVIII | 0.85 | 12 | nd |
| FIX | 0.95 | 91 | 60 |
| FX | 0.92 | 92 | 61 |
| total protein | 72 mg/ml | nd | 0.4 |
| S.A. specific activity (U FIX/mg protein) | | | 1.9 |

TABLE 18

Batchwise adsorption of 20–60 ml with plasma pretreated with DEAE-Sephadex A 50 on 2 ml affinity matrix: FVIII:C and total protein (average values of 3 experiments).

| Sepharose CL4B ligand/spacer/code | LD umoles/ml | plasma ml | FVIII:C (%) ADS | FVIII:C (%) DES | yield U/kg plasma | FVIII:C (U/mg protein) |
|---|---|---|---|---|---|---|
| A4-C4-03.02.87 | 54 | 20 | 98 | 67 | 450 | 4.7 |
|  |  | 40 | 82 | 53 | 440 | 4.9 |
|  |  | 50 | 86 | 42 | 340 | 4.3 |
| DMA3-C5-03.02.87 | 91 | 20 | 98 | 71 | 480 | 2.2 |
|  |  | 40 | 96 | 65 | 530 | 3.3 |
|  |  | 50 | 91 | 55 | 450 | 2.9 |
| A4C-C5-03.02.87 | 54 | 40 | 95 | 49 | 400 | 2.4 |
|  |  | 50 | 94 | 53 | 370 | 2.2 |
|  |  | 60 | 76 | 37 | 310 | 2.5 |

Example 9

Isolation of FII, FIX and FX on DEAE-Sephadex A 50, Followed by Isolation of FVIII/vWF on the Affinity Matrix DMA3-C5-Sepharose CL-4B.04.03.88: Experiment on Larger Scale 100 kg freshly deep-frozen plasma (730 U FVIII:C and 900 U FIX per kg plasma, obtained from the CLB in Amsterdam), was quickly defrosted in a double-walled, stirred tank (wall temperature 40° C.). When the plasma was defrosted and any cryoprecipitate formed was completely dissolved, the tank was cooled (wall temperature 0° C.) until the temperature of the plasma was 15° C. At that moment the temperature was kept constant (wall temperature 15° C). DEAE-Sephadex A 50 (Pharmacia, Sweden), swollen in 150 mM NaCl, was added to the plasma with stirring (0.5 g dry DEAE-Sephadex per l of plasma). The mass was stirred for 60 min. After settling of the DEAE-Sephadex A 50 (standing period 10 min.) the plasma was pumped away from the top of the tank, filtered (20 μm and 0.5 μm filter) and collected in a buffer vessel. The DEAE-Sephadex was withdrawn from the bottom of the vessel and collected in a column (Bio-process 113, Pharmacia, Uppsala, Sweden), washed and desorbed following the procedure described in Example 8. The filtrate obtained after treatment with DEAE-Sephadex A 50, containing FVIII, was contacted with 5 l of the affinity matrix of the type DMA3-C5-Sepharose CL-4B.03.04.88 (ligand density 92 umoles/ml, column BP252, Pharmacia), equilibrated with 170 mM NaCl, 10 mM citrate, 1 mM $CaCl_2$, pH 7.0. After the application of the sample, the affinity matrix was washed with 3 column volumes of 100 mM acetate, 100 mM lysine, 10 mM citrate and 1 mM $CaCl_2$, pH 7.4. Desorption of FVIII was effected with 6 column volumes of 100 mM acetate, 100 mM lysine, 1000 mM NaCl, 10 mM citrate and 1 mM $CaCl_2$, pH 7.4. The flow rate in the column was 30 cm/h. Results are shown in the following Table 19.

TABLE 19

Survey results of large-scale application (100 l plasma) of the method of isolating FII, FVII, FIX and FX on DEAE-Sephadex A 50 (0.5 g/l plasma), followed by the isolation of FVIII/FvWF on affinity matrix DMA3-C5-Sepharose CL4B.0304.88 (LD 92 umoles/ml, 5 l.).

| composition pool (U/ml) | FII 1.07 | FVII 1.00 | FIX 1.05 | FX 1.03 | FVIII:C 0.85 | vWF:Ag 1.0 |
|---|---|---|---|---|---|---|
| DEAE-Sephadex-A50 |  |  |  |  |  |  |
| adsorption (%)* | 87 | 9 | 88 | 89 | 11 | 3 |
| desorption (%)* | 62 | 6 | 69 | 67 |  |  |
| S.A. (specific activity) |  |  |  |  |  |  |
| (U FIX/mg protein) |  |  | 1.8 |  |  |  |
| yield (U/kg plasma) | 663 | 60 | 720 | 690 |  |  |
| DMA3-C5-03.04.88 |  |  |  |  |  |  |
| adsorption (%)** |  |  |  |  | 98 | 95 |
| desorption (%)** |  |  |  |  | 55 | 45 |
| S.A. (specific activity) |  |  |  |  |  |  |
| (U FVIII:C/mg protein) |  |  |  |  | 1.9 |  |
| yield (U/kg plasma) |  |  |  |  | 400 | 410 |

*relative to the quantity in the fresh plasma.
**relative to the quantity in the 0.5 um filtrate.

We claim:

1. A process for isolating coagulation factors from a starting material by means of liquid chromatography, comprising the step of adsorbing said coagulation factors on an adsorbent material comprising a polymeric carrier material to which ligands selected from the group consisting of primary, secondary, tertiary and quarternary amino groups, are linked via spacers, said spacers having a chain length of at least 6 atoms and containing within said chain at least one link having hydrophilic properties and wherein the ligand density is greater than 30 umoles/ml of swollen matrix.

2. A process as claimed in claim 1, comprising spacers which satisfy the generic formula 1:

$$-(CH_2)_m-CO-NH-(CH_2)_n- \qquad (1)$$

in which m and n represent integers having a value of 1–6 and m+n is at least 4.

3. A process as claimed in claim 1, characterized in that the carrier material comprises a hydroxyl groups containing polymeric material, to which the spacers are linked through coupling groups having formula 2:

—CO—NH— (2)

4. A process as claimed in claim 1, characterized in that the carrier material is an agarose.

5. A process as claimed in claim 1, characterized in that the ligands are primary amino groups.

6. A process as claimed in claim 1, characterized in that the ligand density is at least 50 umoles/ml of swollen matrix.

7. A process as claimed in claim 1, characterized by the adsorption stage, further comprising an equilibration buffer and liquid starting material having a specific conductivity below 20 mS/cm.

8. A process as claimed in claim 7, wherein the specific conductivity of the equilibration buffer and liquid starting material are from 13–16 mS/cm.

9. A process as claimed in claim 1 characterized by using a matrix:starting material volume ratio of less than 1:8.

10. The process as claimed in claim 9 wherein the matrix:starting material volume ratio is from 1:12 to 1:20.

11. A process as claimed in claim 1, characterized in that elution is realized by increasing the conductivity of the buffer.

12. The process as claimed in claim 11 wherein the conductivity of the buffer is increased by the addition of sodium chloride.

13. A process as claimed in claim 1, characterized by maintaining a pH in the range of from 6 to 8.

14. The process as claimed in claim 13 wherein the pH is maintained at about pH 7.

15. An adsorbent material having an adsorbent capacity for coagulation factors sufficient to isolate them from blood plasma comprising a polymeric carrier material to which ligands consisting of primary, secondary, tertiary or quaternary amino groups are linked through spacers, said spacers having a chain length of at least 6 atoms and contain within the chain at least one link having hydrophilic properties, the ligand density being in excess of 30 umoles/ml of swollen matrix.

16. An adsorbent material as claimed in claim 15, characterized in that the ligand density is higher than 50 umoles/ml of swollen matrix.

17. An adsorbent material as claimed in claim 15, characterized in that the spacers satisfy the generic formula 1:

$$-(CH_2)_m-CO-NH-(CH_2)_n- \quad (1)$$

wherein m and n represent integers having a value of 1–6 and m+n is at least 4.

18. An adsorbent material as claimed in claim 15, characterized in that the carrier material is a hydroxyl groups containing polymeric material to which the spacers are linked through coupling groups having formula 2:

—CO—NH— (2).

19. An adsorbent material as claimed in claim 15, characterized in that the carrier material is an agarose.

20. An adsorbent material as claimed in claim 15, characterized in that the ligands are primary amino groups.

* * * * *